(12) United States Patent
Habbel

(10) Patent No.: US 8,673,235 B2
(45) Date of Patent: Mar. 18, 2014

(54) SCONCE FOR A FRAGRANCE DISPENSER

(75) Inventor: Sam Habbel, Scottsdale, AZ (US)

(73) Assignee: Arizona Air-Scent, Inc., Scottsdale, AZ (US)

( * ) Notice: Subject to any disclaimer, the term of this patent is extended or adjusted under 35 U.S.C. 154(b) by 549 days.

(21) Appl. No.: 12/927,591

(22) Filed: Nov. 18, 2010

(65) Prior Publication Data

US 2011/0114746 A1    May 19, 2011

Related U.S. Application Data

(60) Provisional application No. 61/281,561, filed on Nov. 19, 2009.

(51) Int. Cl.
*A61L 9/00* (2006.01)
*B01D 47/00* (2006.01)
*A24F 25/00* (2006.01)

(52) U.S. Cl.
USPC ........ 422/306; 261/30; 261/DIG. 65; 239/57; 239/60

(58) Field of Classification Search
USPC ................. 422/5, 124, 306; 261/30, DIG. 65; 239/34, 54, 57, 60
See application file for complete search history.

(56) References Cited

U.S. PATENT DOCUMENTS 4,857,240 A * 8/1989 Kearnes et al. ................. 261/26

* cited by examiner

*Primary Examiner* — Monzer R Chorbaji
(74) *Attorney, Agent, or Firm* — Paul Bogdon

(57) ABSTRACT

A dispenser assembly for supporting a fragrance control unit comprising a canister and a controller or comprising a wafer support plate, fragrance wafers and a fan unit are disclosed. The controller includes a timer, a computer program for the dispersing rate, and a mechanism for activating a spray mechanism of the canister. An embodiment includes a back plate pivotally connected to a front sconce cover and having a tapered structure. Further embodiments include a sconce cover and back plate wherein studs in the sconce cover enter the back plate and the sconce cover is slid upwardly along the back plate and secured in place. Slits in the sconce cover and a top opening allows dispersion of the fragrance. Further embodiments include a sconce cover hinged to the back plate. The sconce cover includes logos and/or decorative designs, e.g. bronco, Southwestern pottery and floral arrangements with slits for dispersing the fragrance.

19 Claims, 8 Drawing Sheets

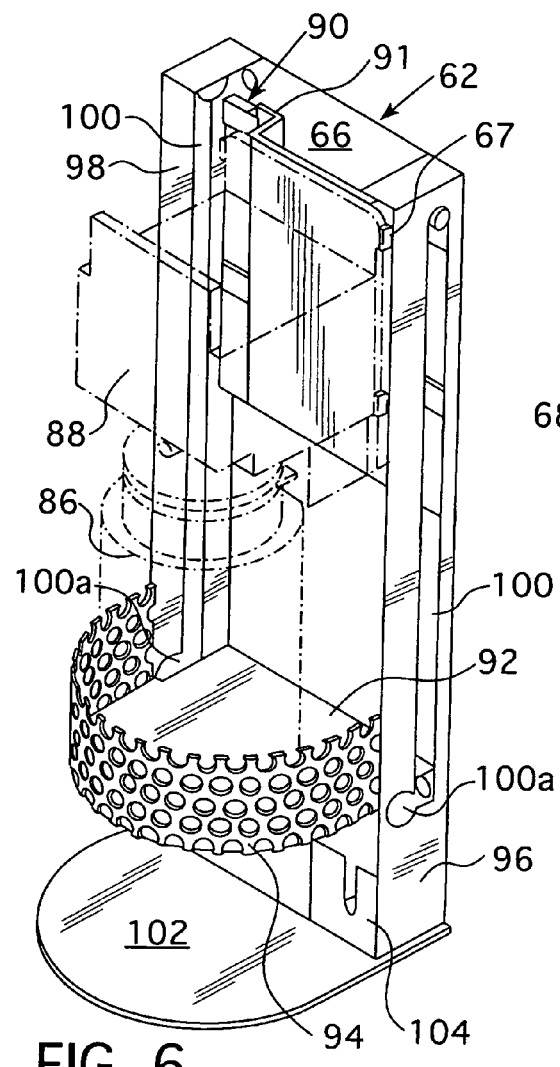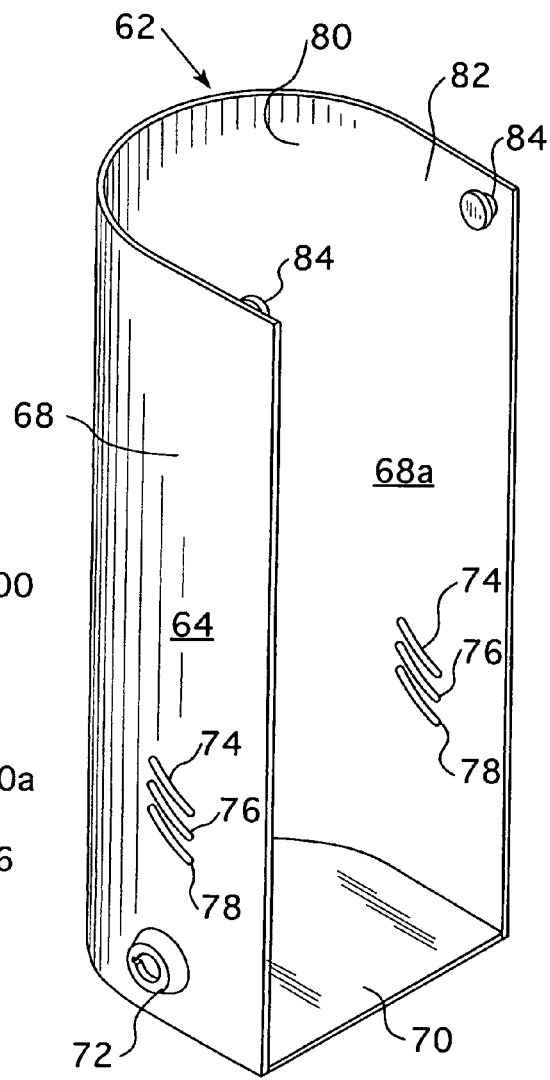

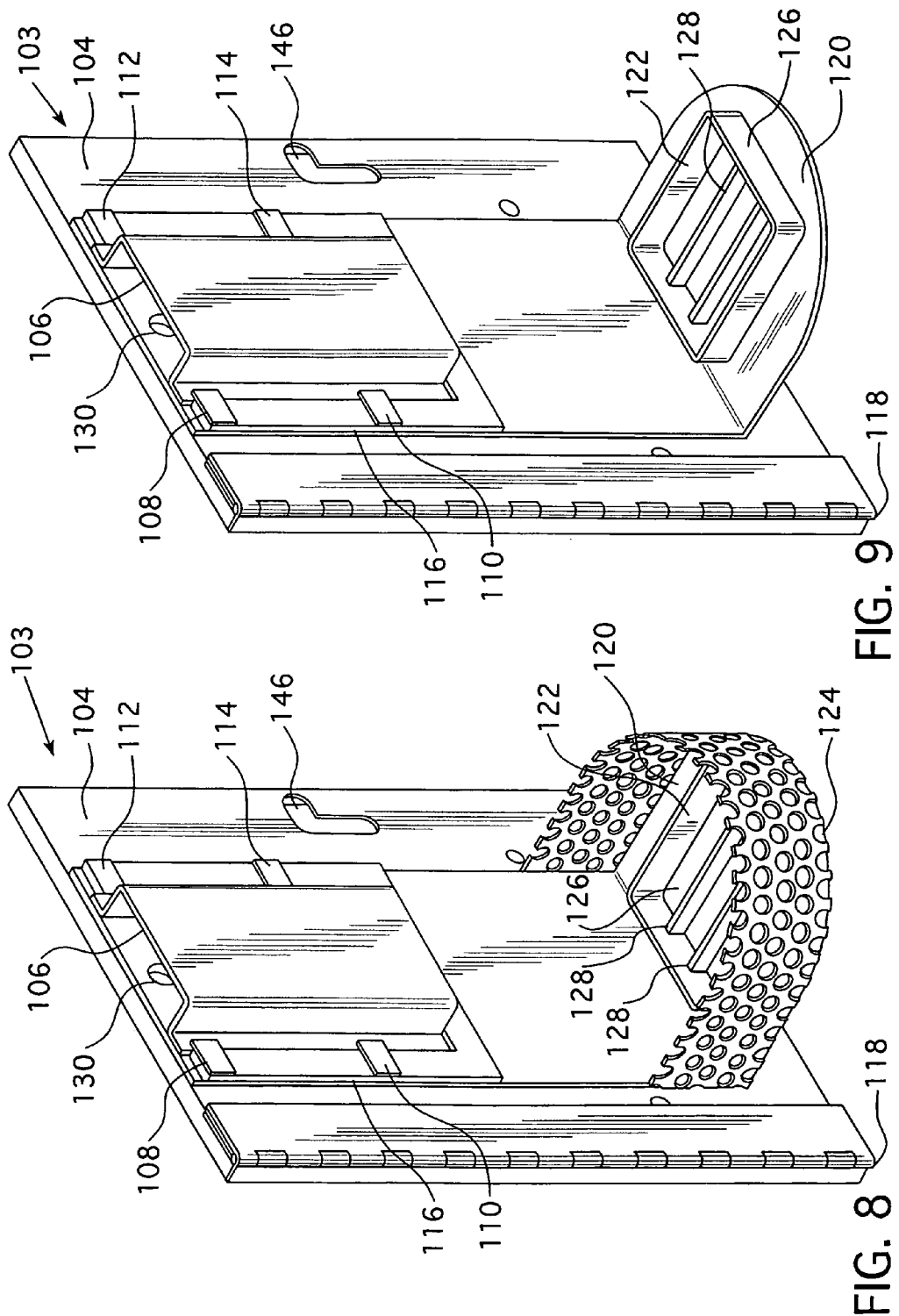

SCONCE FOR A FRAGRANCE DISPENSER

CROSS-REFERENCE TO RELATED APPLICATIONS

This application claims priority to U.S. Provisional Patent Application Ser. No. 61/281,561, filed Nov. 19, 2009, the disclosure of which is incorporated herein by reference in its entirety.

BACKGROUND OF THE INVENTION

1. Field of the Invention

The invention relates to a dispenser assembly for dispersing a fragrance into the atmosphere. More particularly, the invention relates to a dispenser assembly comprising a sconce cover for housing a fragrance control unit, and which sconce cover optionally contains a decorative design and/or a logo.

2. Description of Related Art

Deodorizers are currently used to deodorize commodes and urinals, particularly in the restrooms of institutions and places frequented by the public, although they may also be used in homes. Deodorizer cabinets or frames are generally provided for such deodorizers. Examples of such cabinets or frames are disclosed in U.S. Pat. Nos. 5,533,705; 5,816,846; and 6,105,916. These dispensers provide a drive selectively using a large or small motor providing an air stream for generating vapor from a wick, ceramic wafers, or discs containing vaporizable deodorant and reversible drive mounting mounted back-to-back. U.S. Pat. No. 6,957,779 discloses a framed fluid delivery device that includes a fluid delivery cartridge for the timed release delivery of a fluid. These known deodorant dispensers are commonly used and recognized by the public because of their use for dispersing fragrances in hostile environments, such as restrooms where it is desirous to control the nature of the atmosphere.

It has become desirable to spray and/or disperse a fragrance into other public places, for example, restaurants, coffee houses, airports, convention centers, shopping centers, theaters, and the like in a manner to produce a pleasant environment and to provide a decorative cabinet or frame.

SUMMARY OF THE INVENTION

An aspect of the invention is to provide a dispenser assembly for supporting a fragrance control unit comprising a canister and a controller. The dispenser assembly further comprises a back plate for supporting the canister and controller and for mounting the dispenser assembly against a wall and a sconce cover for enclosing the fragrance control unit. The fragrance control unit is slidable within the back plate such that the dispenser mechanism can be aligned with an opening in the sconce cover so that a stream of fragrance can be directly dispersed from the fragrance control unit and into the atmosphere. The controller further comprises a timer for intermittently dispersing the stream and optionally a computer program for dispersing a desired number of streams per minute or hour. The controller also comprises a mechanism for activation of the spray dispenser of the canister. The sconce cover is pivotally connected at the bottom to the back plate. The sconce cover has a tapered configuration from the bottom to the top and an upper tubular key cam lock and lock catch assembly, and in some embodiments, may be made of powdered coated carbon steel construction.

A further aspect of the invention is to provide a dispenser assembly for supporting a fragrance control unit comprising a canister and a controller, wherein the dispenser assembly includes a back plate for supporting the canister and controller and for mounting the dispenser assembly against a wall, and a sconce cover for enclosing the fragrance control unit. The sconce cover and the back plate are constructed so that studs in the sconce cover enter into apertures of the back plate and the sconce cover is slid upwardly along the back plate and is secured in position via a tubular key cam lock and lock catch assembly. Several openings in the cylindrical housing of the sconce cover and an opening in the top of the dispenser assembly disperses the fragrance into the environment.

A still further aspect of the present invention is to provide a dispenser assembly for supporting a fragrance control unit comprising a canister and a controller or alternately for supporting a fragrance control unit comprising a wafer nest including fragrant wafers and a fan unit which is used to generate and disperse a fragrance from the wafers and into the environment. A sconce cover is hinged to one longitudinal side of a back plate and is secured to the back plate via a tubular key cam lock and lock catch assembly. The sconce cover may comprise one or more decorative designs and/or company logs having slits with the same configuration as the decorative design and/or logo and which slits allow the fragrance to be dispersed, and further includes an aperture for directly dispersing a stream of fragrance out into the environment.

The controller of the fragrance control unit may include a timer, a computer program for controlling the dispersing rate, and a dispersing mechanism for activating the spray mechanism of the canister. The fragrance control unit may alternately comprise a fan unit, a wafer holder plate, and fragrance wafers supported on the wafer holder plate.

Designs for the sconce cover may include a bronco cowboy riding a bull, a Southwestern pottery arrangement, and different floral arrangements, all of which have one or more slits outlining the artistic design for dispersing fragrance into the environment. Logos may also be included on the sconce cover containing slits for dispersing fragrance into the environment.

These and other aspects of the invention will be better appreciated and understood when the following description is read in light of the accompanying drawings.

DESCRIPTION OF THE DRAWINGS

FIG. 6 is a right perspective view of a dispenser assembly of a further embodiment of the present invention showing in phantom a liquid fragrance canister and a controller for intermittently operating the canister so that a stream of liquid is dispersed from the canister.

FIG. 7 is a rear left perspective view of a sconce cover for the dispenser assembly of FIG. 6.

FIG. 8 is a left perspective view of a back plate of a dispenser assembly of a further embodiment of the present invention.

FIG. 9 is a left perspective view of a back plate of a dispenser assembly similar to that of FIG. 8.

DESCRIPTION OF THE INVENTION

Figure 1:
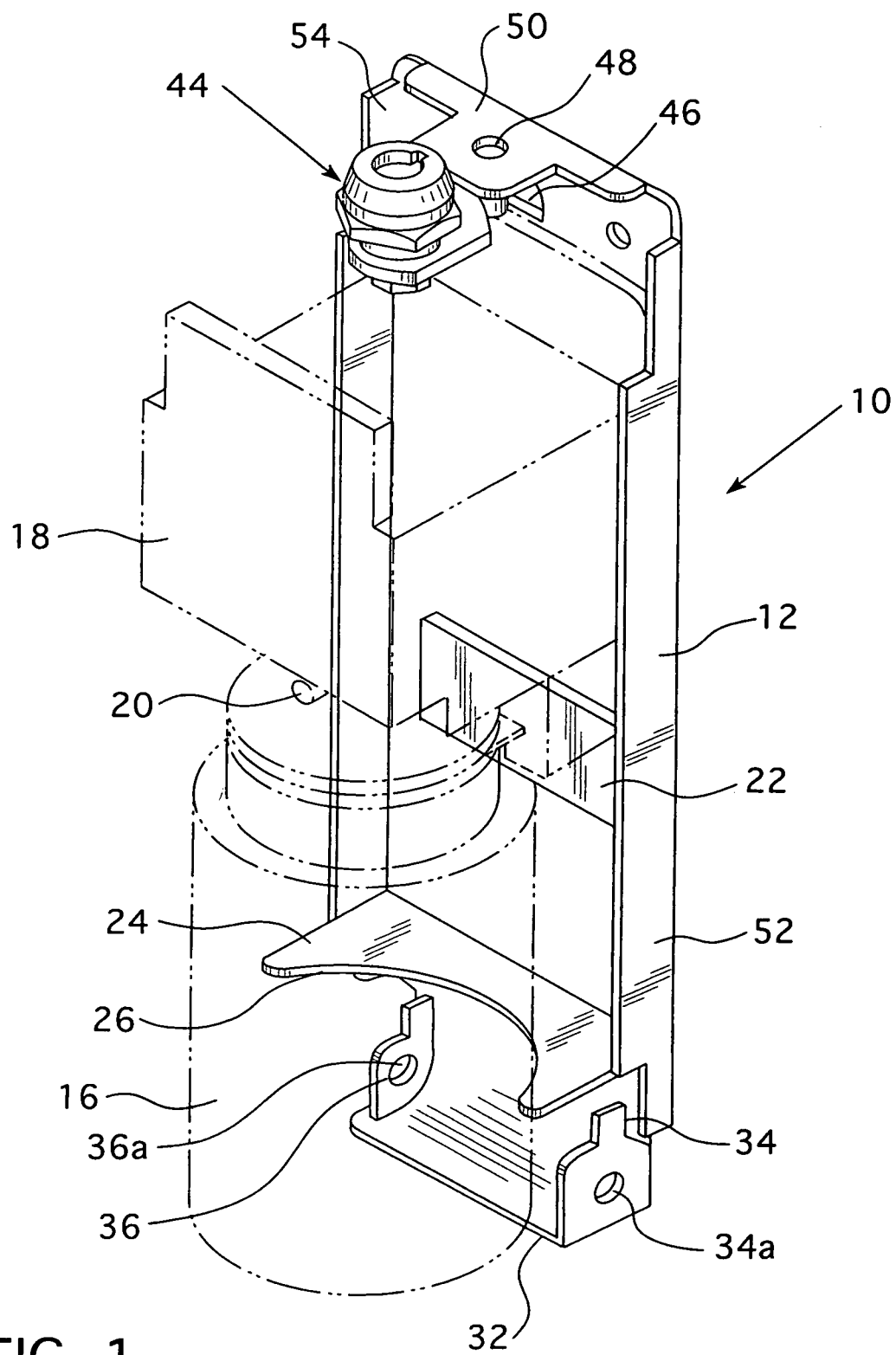
FIG. 1 is a right perspective view of a dispenser assembly of an embodiment of the present invention showing in phantom a canister containing a liquid fragrance and a controller for intermittently operating the canister so that a stream of liquid is dispersed from the canister.
Figures 2, 3:
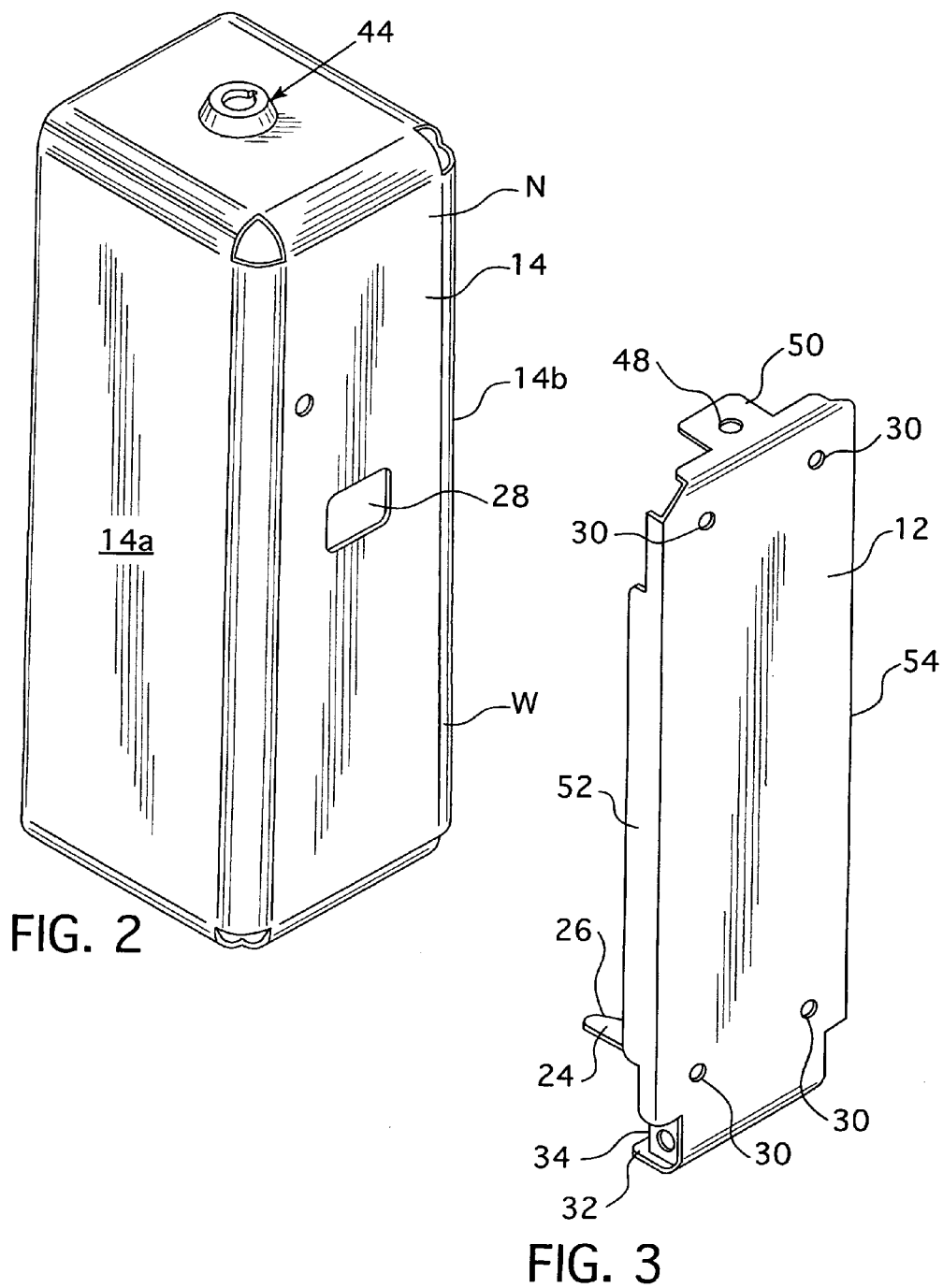
FIG. 2 is a front left perspective view of a sconce cover for the dispenser assembly of FIG. 1.
FIG. 3 is a rear left perspective view of the back plate of the dispenser assembly of FIG. 1.

FIGS. 1, 2, 3, 4 and 5 refer to a first embodiment of a dispenser assembly 10 of the present invention. Dispenser assembly 10 comprises a back plate 12 (FIGS. 1 and 3) and a sconce cover 14 (FIGS. 2 and 4), which as shown in FIG. 2 forms a tapered body with a wide portion W at the bottom and a narrow portion N at the top of FIG. 2. Preferably, dispenser assembly 10 is of a powder coated carbon steel construction. As shown in FIG. 1, dispenser assembly 10 further comprises a fragrance control unit, which, in turn comprises a canister 16 which contains a liquid fragrance and a controller 18. Canister 16 and controller 18 are shown in phantom for a better understanding of the construction of dispenser assembly 10. In general, controller 18 will comprise a timer (not shown) and a mechanism (not shown) for activating a spray dispenser of canister 16. In some embodiments, the timer may include a computer program for delivering a desired number of fragrant sprays per minute or hour. Canister 16 and controller 18 are elements that are available commercially and therefore details of these components are not necessary for a full understanding of the invention. Canister 16 in general has a spray dispenser 20 (FIG. 1) for spraying and/or dispersing a fragrance. Controller 18 has an underside configuration that corresponds to the upper portion of canister 16 so that these two components 16 and 18 are nested together when canister 16 is inserted into the back plate 12 and into controller 18 and canister 16 interlocks with controller 18 such that canister 16 is suspended from controller 18. A member 22 is provided for anchoring controller 18 into back plate 12.

A canister support member 24 is provided in back plate 12 to both support and space canister 16 away from back plate 12. Canister support member 24 has an arcuate surface 26 corresponding to an outer arcuate surface of canister 16 for spacing canister 16 away from back plate 12. Canister 16 and controller 18 are slid within back plate 12 in order to position spray dispenser 20 (FIG. 1) in alignment with an opening 28 of sconce cover 14 (FIG. 2). Even though not shown, an elongated tube may be attached to spray dispenser 20 so that it extends out of opening 28 for directing a fragrance spray out of sconce cover 14 of dispenser assembly 10.

Figure 4:
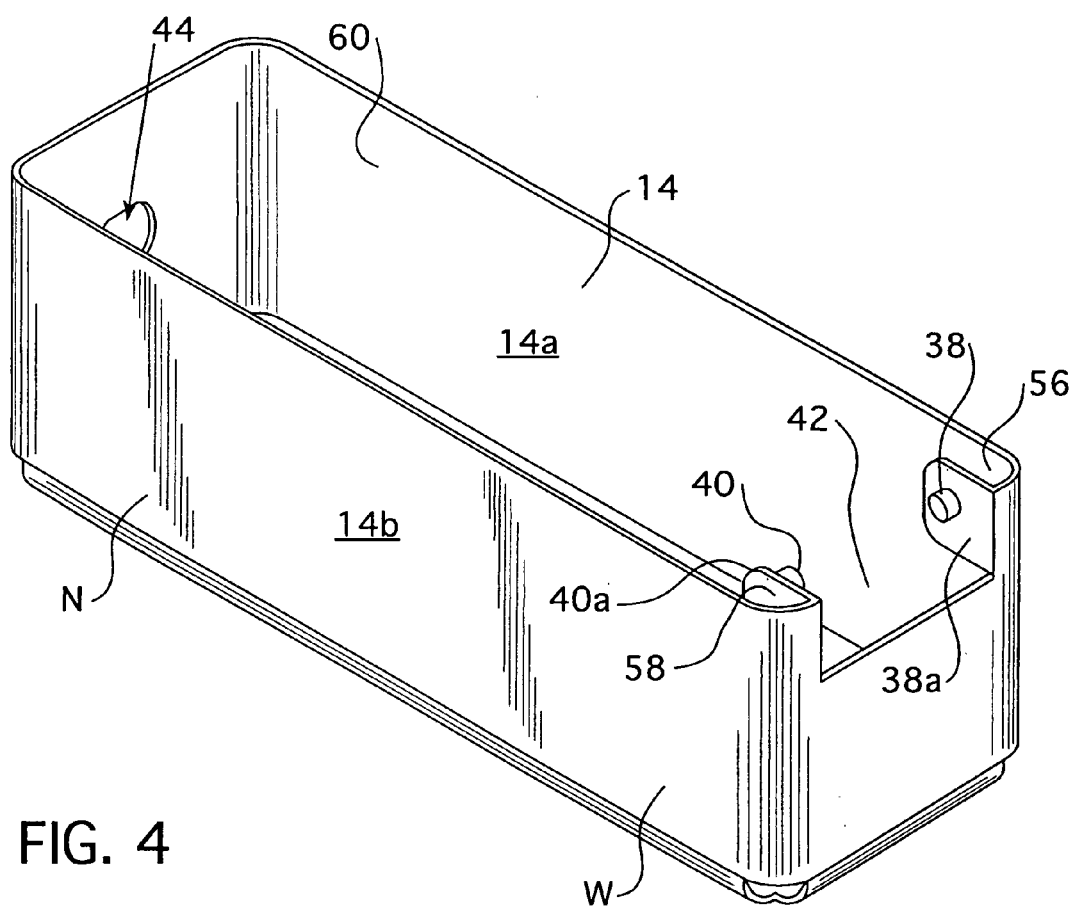
FIG. 4 is a rear perspective view of the sconce cover of FIG. 2 lying on its front surface.

As particularly shown in FIG. 3, back plate 12 includes several openings 30 for attaching back plate 12 and therefore dispensing assembly 10 to a flat surface, such as a wall, through suitable fastening devices, such as, for example, screws or nails. Referring again to FIG. 1, the lower portion of back plate 12 further comprises a gusset member 32 containing opposed gussets 34 and 36 for pivotally connecting sconce cover 14 to back plate 12. This pivotal connection is made via pins 38 and 40 provided in sconce cover 14 (FIG. 4) and which pins 38, 40 are inserted into apertures 34a and 36a of gussets 34 and 36, respectively. As shown in FIG. 4, sconce cover 14 further comprises a cut-out section 42 located between pins 38 and 40. Sconce cover 14 is connected to back plate 12 by positioning sconce cover 14 such that cut-out section 42 receives gusset member 32 of back plate 12 and pins 38 and 40 enter into the apertures 36a and 34a of gussets 36 and 34, respectively.

Figure 5:
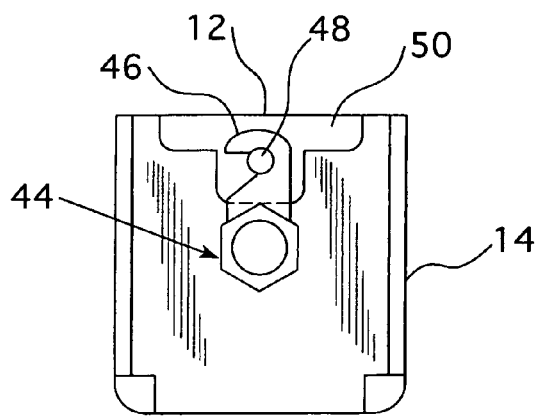
FIG. 5 is top sectional view showing a lock pawl of a key cam lock and lock catch assembly of the sconce cover in engagement with a pin of the back plate of FIG. 1.

Sconce cover 14 is located and secured to the top of back plate 12 via a tubular key cam lock and lock catch assembly 44 shown best in FIG. 1. Key cam lock and lock catch assembly 44 comprises a lock pawl 46. Lock pawl 46 is rotated via rotation of key cam lock and lock catch assembly 44 and engages a lock catch pin 48 in a bracket 50 of back plate 12. This structure is also shown in FIG. 5. Tubular key cam lock and lock catch assembly 44 requires a key for operation. Tubular key cam lock and lock catch assembly 44 is commercially available and its operation is well-known to those skilled in the art.

Back plate 12 further comprises opposed longitudinal side brackets 52 and 54 as shown in FIG. 1, and sconce cover 14 further comprises members 38a and 40a which contain pins 38 and 40, respectively. Member 38a forms a recess 56 with sidewall 14a of sconce cover 14 and member 40a forms a recess 58 with sidewall 14b of sconce cover 14 as shown in FIG. 4. When back plate 12 and sconce cover 14 are assembled together, side brackets 52 and 54 of back plate 12 enter into recesses 58 and 56 respectively, and bracket 50 of back plate 12 is received in the opened area 60 of sconce cover 14 so as to provide a substantially enclosed dispensing assembly 10. Rotation of key cam lock and lock catch assembly 44 by a key (not shown) will cause lock pawl 46 to engage catch pin 48.

FIGS. 6 and 7 illustrate a further embodiment of a dispenser assembly of the invention. Dispenser assembly 62 comprises a sconce cover 64 and a back plate 66 wherein sconce cover 64 is slidable within and along back plate 66. Preferably, dispenser assembly 62 is of a powder coated carbon steel construction. With reference to FIG. 7, sconce cover 64 comprises a body 68 having a curved configuration; a lower portion 70 attached to body 68 through suitable means, such as for example, tack welding; a tubular key cam lock and lock catch assembly 72; slits or openings 74, 76 and 78 on opposed sides of body 68; and an opened upper portion 80. Upper portion 82 of body 68 further includes two opposed studs 84, each of which is attached to an inner surface 68a of body 68 of sconce cover 64, through suitable means, such as by welding.

Referring particularly to FIG. 6, back plate 66 supports a fragrance control unit which comprises a canister 86 and a controller 88, which are shown in phantom for a better understanding of construction of dispenser assembly 62. In a manner similar to that described for the dispenser assembly 10 of FIGS. 1 through 5, canister 86 and controller 88 of dispenser assembly 62 of FIGS. 6 and 7 are nested together as a unit. Back plate 66 further includes a bracket assembly 90, a support member 92, and a flange 94. As shown in FIG. 6, bracket assembly 90 includes a U-shape plate member 91 which extends across back plate 66 for supporting controller 88, and support member 92 and flange 94 support canister 86. Bracket assembly 90 is structured to interchangeably support controller 88 as shown in FIG. 6 or a fan unit which would be used in conjunction with wafers supported on a wafer holder plate, the latter of which would be supported by support member 92 in a fashion similar to that disclosed herein below with reference to FIGS. 8 and 9. Controller 88 is slidable along bracket assembly 90 for a desired positioning in back plate 66 and the positioning of canister 86 within flange 94. A sliding mechanism 67 (FIG. 6) may be provided for this purpose.

Still referring to FIG. 6, back plate 66 further includes two spaced apart longitudinal flanges 96 and 98, each of which has an elongated channel 100 for receiving a stud 84 of sconce cover 64. That is, for the assemblage of sconce cover 64 and back plate 66, each stud 84 of sconce cover 64 enters into the lower portion 100*a* of elongated channels 100 of flanges 96 and 98, and the sconce cover 64 is slid upwardly until the lower portion 70 of sconce cover 64 abuts against a lower support member 102 of back plate 66. As indicated in FIGS. 6 and 7, lower portion 70 of sconce cover 64 and lower support member 102 of back plate 66 have a similar configuration such that sconce cover 64 fits tightly against back plate 66. As shown in FIG. 6, back plate 66 also includes a lock catch member 104 which is engaged by an L-shaped pawl (not shown) of tubular key cam lock and lock catch assembly 72 of sconce cover 64 in a manner well known to those skilled in the art.

As disclosed herein above, in some embodiments, the dispenser assembly 62 of FIGS. 6 and 7 may optionally comprise a fragrance control unit that comprises a fan unit, wafers and a wafer holder plate, in which instance, the wafer holder plate would be supported by support member 92 and the fan unit would be supported by bracket assembly 90. In this instance, the fan unit would be operated to generate and/or circulate a fragrance from the fragrant wafers supported on the wafer holder plate such that the fragrance can be delivered up through the opened upper portion 80 and/or through slits 74, 76 and 78 of sconce cover 64. Similar to the embodiment of FIGS. 1-5, back plate 66 may be mounted against a wall via one or more openings in back plate 66 in which suitable fastening means, for example, screws or nails are inserted. The plurality of slits 74, 76 and 78 on each side of sconce cover and the opened upper portion 80 of the sconce cover cooperate to create an air flow for the fragrance emanating from the fragrance control unit of dispenser assembly 62.

FIGS. 8, 9, 10, 11, 12, 13 and 14 illustrate further embodiments for a dispenser assembly of the invention. FIGS. 8-11 illustrate a dispenser assembly 103. Referring particularly to FIGS. 8 and 9, dispenser assembly 103 comprises a back plate 104 which comprises a U-shape module mount plate 106; a plurality of retainer strips 108, 110, 112 and 114 for retaining the U-shape module mount plate 106; a U-shape back spacer 116 mounted between the retainer strips 108-114 and the back plate 104; a hinge 118 along the longitudinal edge of the back plate 104; a support member 120 projecting outwardly from the back plate 104; a wafer support plate 122 supported by the support member 120 for supporting fragrance wafers (not shown); and a flange support 124 connected to the periphery of support member 120.

As illustrated in FIG. 8, flange support 124 may have a plurality of apertures which may be in the pattern shown therein so as to enhance the air flow through the dispenser assembly 103. Wafer support plate 122 comprises a wafer enclosure plate 126 and a wafer divider 128. If back plate 104 supports a wafer support plate 122, then, even though not shown, module mount plate 106 will, in some embodiments, support a fan unit for generating and dispersing fragrance from the wafers and into the atmosphere in a manner well known to those skilled in the art. In this latter instance, the fan unit, the wafer support plate 112 and the wafers will constitute a fragrance control unit. In some embodiments, if the fragrance control unit comprises a controller and a canister as illustrated in phantom in FIG. 12, then the controller can be inserted down into the U-shape back spacer 116 and between retainer strips 108-114 as particularly illustrated in FIG. 12.

In some embodiments, if the fragrance control unit comprises a fan unit and a wafer plate support containing fragrance wafers, then the fan unit will be mounted to the U-shape module mount plate 106 in a manner apparent to those skilled in the art. Back plate 104 may be mounted to a wall via one or more apertures 130 and suitable fasteners, such as, for example, clips, nails and/or screws.

Figure 11:
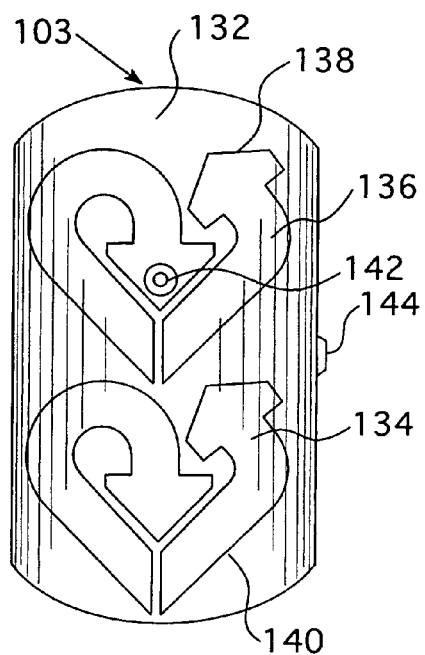
FIG. 11 is a front view of the sconce cover of FIG. 10.
Figure 10:
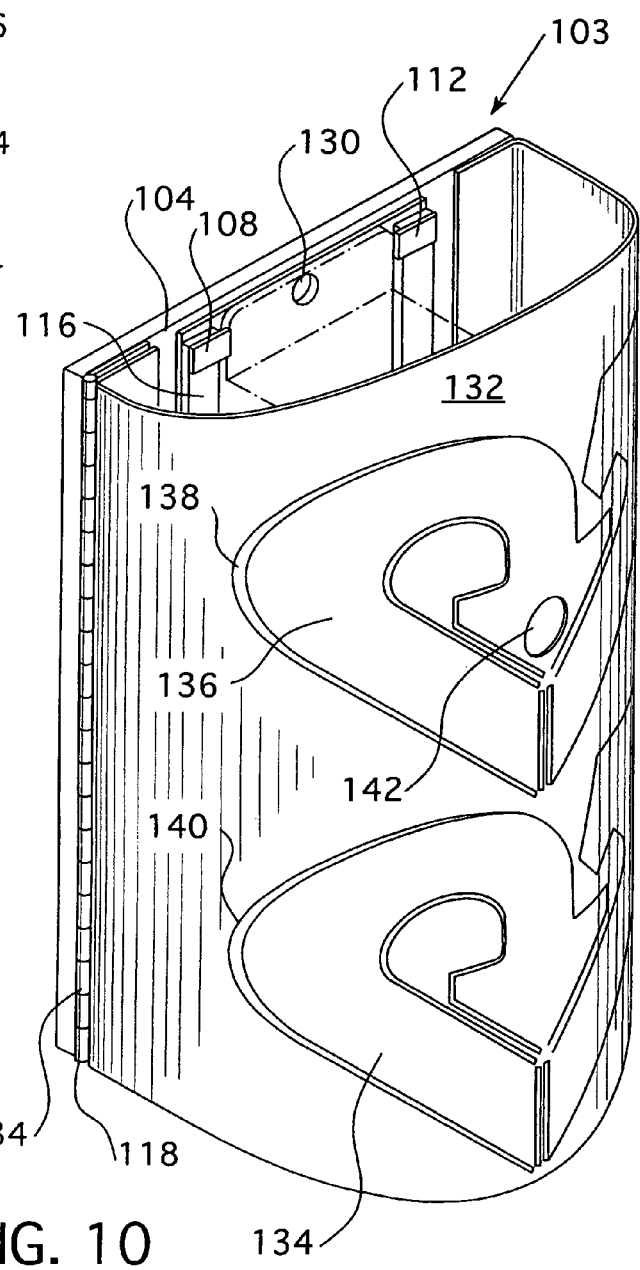
FIG. 10 is left perspective view of a sconce cover having a decorative design and which sconce cover may be used in the dispenser assembly of FIGS. 8 and 9.

A suitable sconce cover for the dispenser assembly 103 of FIGS. 8 and 9 is shown at reference numeral 132 in FIGS. 10 and 11. Sconce cover 132 comprises a corresponding hinge 134 which interconnects with hinge 118 of back plate 104 for connecting sconce cover 132 to back plate 104. Sconce cover 132 has a curved configuration and comprises decorative designs 134 and 136. Decorative designs 134, 136 include slits 138, 140 which have a configuration corresponding to that of decorative designs 134 and 136 and which slits 138, 140 outline the decorative designs 134 and 136 for creating an air flow for the fragrance emanating from the fragrance control unit for dispersing a fragrance into the environment. The dispenser assembly 103 of FIGS. 8-11 may also support a canister and a controller similar to that disclosed for the dispenser assembly 10 of FIGS. 1-5 and dispenser assembly 62 of FIGS. 6-7. If the dispenser assembly 103 of FIGS. 8-11 supports a canister and a controller for controlling the rate of fragrance dispensed from the canister similar to that disclosed for the dispenser assemblies 10, 62 of FIGS. 1-7, then an aperture 142 (FIGS. 10 and 11) is provided in sconce cover 132 for delivering a direct stream of fragrance through sconce cover 132.

Figure 12:
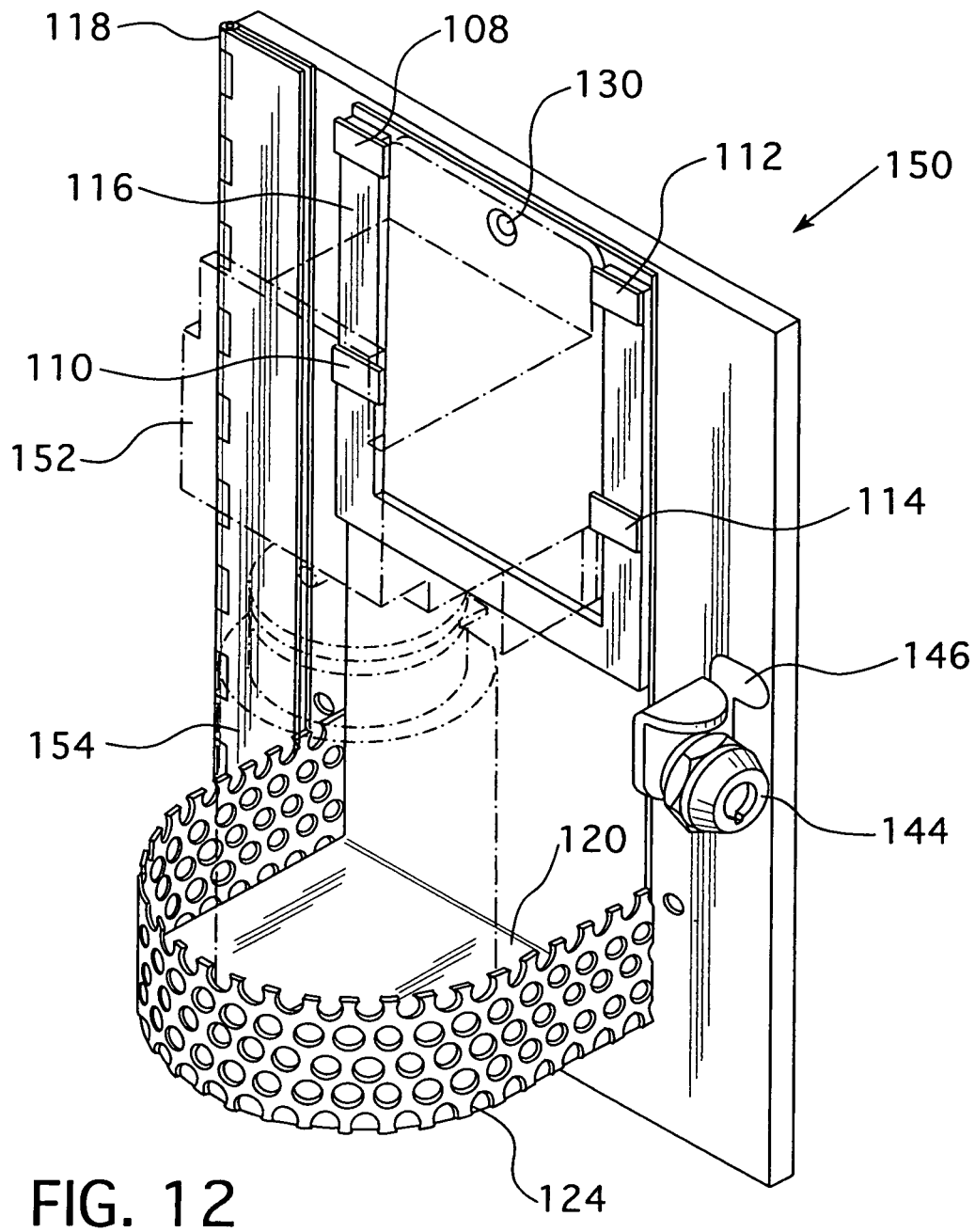
FIG. 12 is a right perspective view of a back plate of a dispenser assembly comprising a liquid fragrance canister and a controller (in phantom) for intermittently operating the canister so that a stream of liquid is dispersed from the canister.

Even though not shown in FIGS. 8-11, a tubular key cam lock and lock catch assembly similar to that provided at reference number 144 in the embodiment of FIG. 12 will be provided. In this instance, the tubular key cam lock and lock catch assembly will comprise a lock latch (not shown) for entering into the L-shaped opening 146 in back plate 104 (FIGS. 8 and 9). When sconce cover or shield 132 is attached to back plate 104, the sconce cover 132 covers the fragrance control unit in a spaced away relationship and allows the fragrance to be dispersed out into the environment through slits 138, 140 and/or through aperture 142 (FIGS. 10 and 11).

Figures 13, 14:
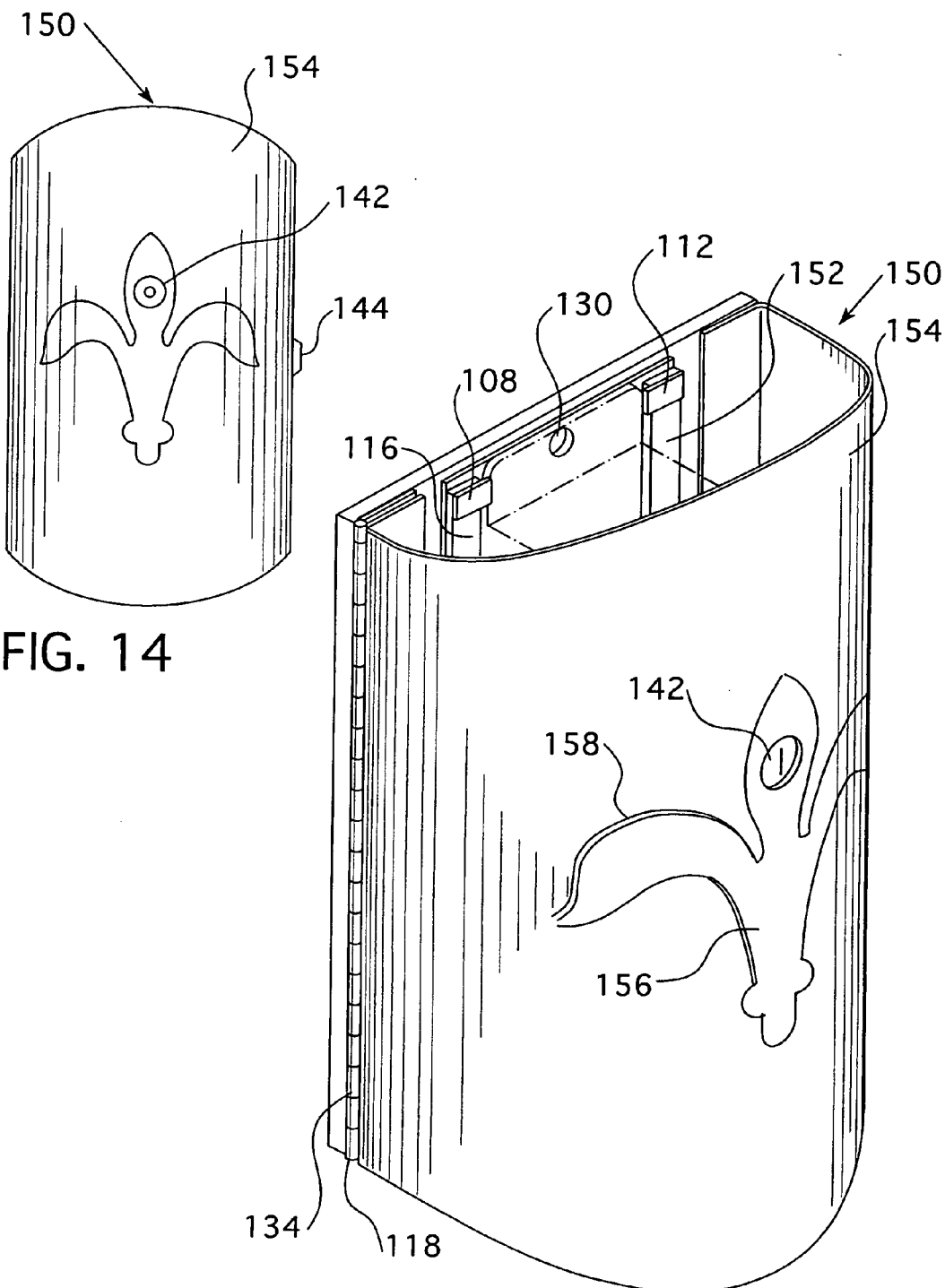
FIG. 13 is a left perspective view of a sconce cover having a decorative design different from that of FIGS. 10 and 11 which may used in the dispenser assembly of FIGS. 8 and 9.
FIG. 14 is a front view of the sconce cover of FIG. 13.

FIGS. 12-14 illustrates a further embodiment of a dispenser assembly 150. As shown in FIG. 12, dispenser assembly 150 supports, as shown in phantom, a canister 154 and a control box 152 which constitutes a fragrance control unit, and which fragrance control unit may be similar to that described herein above with reference to the other embodiments of the invention. In FIGS. 12-14, like numerals represent like components illustrated in FIGS. 8 through 11.

A suitable sconce cover 154 for the embodiment of FIG. 12 is illustrated in FIGS. 13 and 14. Sconce cover 154 has a curved configuration and contains a decorative design 156. Decorative design 156 has slits 158 that corresponds to and outline the decorative design 156. It is to be appreciated that sconce cover 154 of FIGS. 13 and 14 can be interchangeable with the sconce cover 132 of FIGS. 10 and 11.

In the embodiments of FIGS. 10 and 13, sconce covers 132 and 154, respectively, are opened at the top and bottom. In some embodiments, this structure for sconce covers 132, 154 allows an undercurrent of air to flow upwardly into the dispenser assembly 130, 150 and through the slits of sconce cover 132, 154; however, the clearance between the back plate and the sconce cover is such that the inside of the dispenser assembly is not accessible other than through the unlocking of the key cam lock and lock catch assembly. In some embodiments, sconce covers 132 and 154 may be made of an aesthetic metal sheet, for example, a brushed metal sheet or a copper sheet. In some embodiments, the slits in the sconce covers 132 and 154 may be made using an etching method. In some embodiments, the sconce covers 132 and 154 may be attached to their respective back plate through suitable fasteners along their opposed longitudinal edges or along the longitudinal edges of the back plate. In some embodiments, the sconce covers 132 and 154 may include cut-outs, designs and/or logos that are centrally located and slits along their sides similar to slits 74, 76 and 78 of sconce cover 68 of FIG. 7.

Even though the embodiments of FIGS. 8-14 illustrate a sconce cover as being attached to the back plate via a hinge arrangement, it is to be appreciated that the sconce cover may be attached to the back plate through other appropriate fastening means. For example, the sconce cover may be attached by using a fastening arrangement, for example, clips, screws and/or nails, provided along the opposed longitudinal sides of the sconce cover and the back plate. In this instance, the back plate may first be attached to the wall and the sconce cover than attached to the back plate.

The spray dispenser or aerosol such as that for example indicated at reference number 20 in FIG. 1 as disclosed herein above may have an elongated tube which extends outwardly from aperture 28 of sconce cover 14. In some embodiments of the invention one or more such elongated tubes may be provided for delivering the liquid fragrance into one or more directions outwardly from the sconce cover wherein the elongated tubes may be bent in such directions for delivering the liquid fragrance into one or more desired pathways outwardly from the sconce cover.

In some embodiments of the invention, a sliding mechanism similar to that illustrated in FIG. 6 may be provided in the back plate of the dispenser assembly of the several embodiments of the invention and this sliding mechanism may be structured and arranged to accommodate the different types of controllers and/or fan units of the fragrance control unit of the invention. In some embodiments, the, designs, motifs, cut-outs and/or logos provided in the sconce cover may be custom made. In some embodiments, the sconce cover may be made of an aesthetic metal sheet, for example, a brushed metal sheet or a copper sheet. In some embodiments, the slits in the sconce cover may be made using an etching method. In the embodiments of the invention, the canister and the controller and the fan unit, wafer support plate and the fragrance wafers of the fragrance control unit are well-known items that are commercially available. In some instances, the fan unit and the controller may be battery and/or electrically operated, and their operation may be controlled through an off/on button. In some embodiments, the fragrance control unit may be provided with a wick, ceramic wafers or discs containing vaporizable deodorant and a drive using a motor providing an air stream for generating vapor from the wick, ceramic wafers, or discs.

While the present invention has been described in connection with the preferred embodiments of the various figures, it is to be understood that other similar embodiments may be used or modifications and additions may be made to the described embodiment for performing the same function of the present invention without deviating there from. Accordingly, it is intended by the appended claims to cover all such changes and modifications as come within the spirit and scope of the invention.

What is claimed is:

1. A dispenser assembly for dispersing fragrance into an environment, comprising:
   an upright back plate member;
   a generally U-shaped module back spacer secured to an upper section of said back plate member;
   a modular mount means selectively secured to and removable from said module back spacer for supporting a fragrance control unit assembly;
   an outwardly extending support member secured to a lower end section of said back plate member; and
   support means secured to said outwardly extending support member for receiving and supporting a source of fragrance.

2. The dispenser assembly of claim 1 wherein the fragrance control unit comprises a canister containing a liquid fragrance and a controller for controlling the dispersing rate of the canister.

3. The dispenser assembly of claim 1 wherein the fragrance control unit comprises a fan unit for generating and dispersing a fragrance into the environment and wherein the source of fragrance comprises at least one fragrance wafer.

4. The dispenser assembly of claim 1 including a sconce cover mounted to said back plate member for inclosing the fragrance control unit assembly and the source of fragrance.

5. The dispenser assembly of claim 4 wherein the sconce cover is pivotally connected to the back plate at the bottom of the sconce cover and wherein the sconce cover swings upwardly to enclose the fragrance control unit on the back plate and the source of fragrance; and wherein the assemblage of the dispenser assembly is in a tapered fashion.

6. The dispenser assembly of claim 5 wherein the sconce cover comprises opposed studs and the back plate comprises opposed apertures; and wherein each of the studs of the sconce cover engage one of the opposed apertures of the back plate member for sliding the sconce cover upwardly and downwardly along the back plate for assembling and disassembling the sconce cover relative to the back plate.

7. The dispenser assembly of claim 4 wherein the back plate member includes a lower portion and wherein the sconce cover includes a lower portion having the same configuration as the lower portion of the back plate member; and wherein the lower portion of the back plate and the lower portion of the sconce cover fits against each other when the sconce cover is assembled to the back plate.

8. The dispenser assembly of claim 7 wherein the sconce cover further comprises a plurality of slits and an opened upper portion for creating an air flow for dispersing the fragrance into the environment.

9. The dispenser assembly of claim 4 wherein the sconce cover is connected to the back plate member along one longitudinal side of the sconce cover and back plate member; wherein the sconce cover is swingable in a horizontal plane relative to the back plate member for opening and closing the dispenser assembly; and wherein the sconce cover and the back plate member comprise a hinge arrangement for connecting the sconce cover to the back plate member along the one side of the sconce cover and for swinging the sconce cover in a horizontal plane for opening and closing the dispenser assembly.

10. The dispenser assembly of claim 9 wherein the sconce cover comprises a curved configuration and a decorative design which comprises slits corresponding to the decorative design for creating an air flow for dispersing a fragrance into the environment.

11. The dispenser assembly of claim 4 wherein the sconce cover comprises a curved configuration and includes at least a decorative design having a slit configuration corresponding to the configuration of the decorative design for creating an air flow for dispersing fragrance into the environment.

12. The dispenser assembly of claim 11 wherein the decorative design includes a bronco cowboy, Southwestern pottery arrangement, and floral arrangements.

13. The dispenser assembly of claim 4 wherein the sconce cover includes at least a logo having a slit configuration corresponding to the configuration of the logo for dispersing fragrance into the environment.

14. The dispenser assembly of claim 4 wherein the dispenser assembly further comprises a tubular key cam lock and lock catch assembly for securing the sconce cover to the back plate.

15. The dispenser assembly of claim 4 wherein the sconce cover further comprises an aperture for delivering a direct stream of fragrance out of the sconce cover.

16. The dispenser assembly of claim 4 wherein the sconce cover comprises a plurality of slits and an upper opening and a lower opening for allowing an undercurrent of air to flow upwardly into the dispenser assembly and through the plurality of slits.

17. The dispenser assembly of claim 1 wherein said module back spacer includes a plurality of retainer strip means arranged for holding said modular mount means in place.

18. The dispenser assembly of claim 1 wherein said module back spacer is shaped for upwardly and downwardly slideably supporting said modular mount means.

19. The dispenser assembly of claim 1 including an enclosure surrounding said support means; and including spaced wafer divider means on said support means for receiving fragrance producing wafers; and further including a perforated flange member fixed to said support member and surrounding said support means.

\* \* \* \* \*